US00PP27169P3

(12) United States Plant Patent
Merrifield

(10) Patent No.: US PP27,169 P3
(45) Date of Patent: Sep. 20, 2016

(54) ASPEN TREE NAMED 'KMN01'

(50) Latin Name: *Populus tremuloides*
Varietal Denomination: KMN01

(71) Applicant: Kevin Earl Merrifield, Bonners Ferry, ID (US)

(72) Inventor: Kevin Earl Merrifield, Bonners Ferry, ID (US)

( * ) Notice: Subject to any disclaimer, the term of this patent is extended or adjusted under 35 U.S.C. 154(b) by 154 days.

(21) Appl. No.: 14/120,618

(22) Filed: Jun. 10, 2014

(65) Prior Publication Data

US 2015/0359152 P1 Dec. 10, 2015

(51) Int. Cl.
*A01H 5/00* (2006.01)

(52) U.S. Cl.
USPC ..... Plt./216

(58) Field of Classification Search
USPC ..... Plt./216
See application file for complete search history.

*Primary Examiner* — Keith Robinson

(57) ABSTRACT

A new and distinct variety of quaking or trembling aspen named 'KMN01' that is characterized by orange to red leaf coloration in the fall-season, an upright branching habit, and disease resistance to *Venturia* leaf and shoot blight. Additionally the new variety is seedless, its spring new growth is bronze to red in coloration, and it has bright white bark.

4 Drawing Sheets

Figure 1:
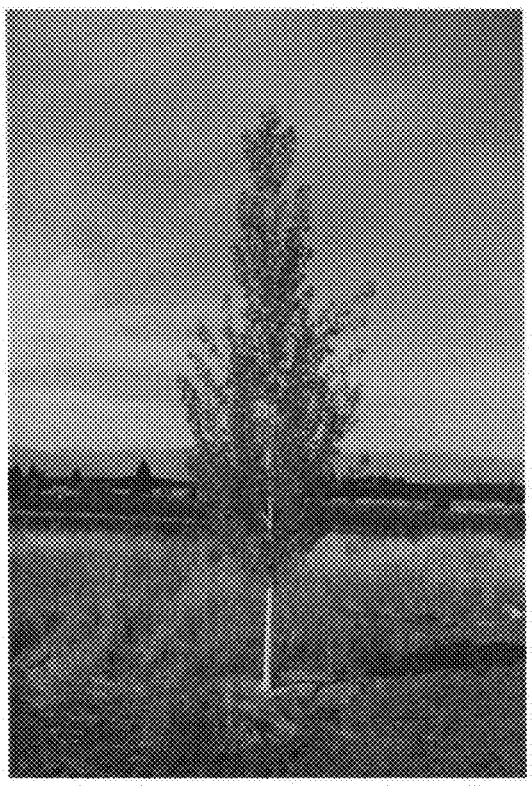

Latin name of the genus and species of the plant claimed: The quaking aspen tree variety of this invention is botanically identified as *Populus tremuloides*.

Variety denomination: The variety denomination is 'KMN01'.

BACKGROUND OF THE INVENTION

The present invention relates to a new and distinct seedless plant variety of *Populus tremuloides*, more commonly known as Trembling Aspen or Quaking Aspen, having orange to red fall-season leaf coloration, an upright branching habit, and disease resistance to *Venturia* leaf and shoot blight.

Trembling Aspen is a deciduous tree with extensive distribution throughout North America. Its adaptation to a variety of soil conditions and elevations contributes to its broad market appeal and utilization where it is a popular landscape feature. Aspen trees encompass a number of similar species that are aesthetically appealing for their fall-season leaf coloration, which typically ranges from yellow to gold. An additional aesthetic feature is the "quaking" sound arising from the wind moving across the flattened petioles. Trembling Aspen are also used in forest reclamation areas, quickly taking root after fires. At which time, they provide habitat while slower growing evergreens repopulate. Trembling Aspen are highly susceptible to *Venturia* leaf and shoot blight.

The new variety, in contrast, demonstrates disease resistance to *Venturia* leaf and shoot blight. It also differs from the more prevalent commercially available aspen wherein 'KMN01' demonstrates orange to red fall-season leaf coloration and its new spring growth is bronze to red in color. This coloration provides a unique aesthetic value to landscaped areas. Typical of the species, the expected maximum height is 25.0 meters, with a lifespan of fifty to sixty years.

'KMN01', discovered and asexually propagated by the inventor, was selected from a cultivated nursery field located in Bonners Ferry, Id. in April 2004. Discovered among a field of unsold *Populus tremuloides* and likely a result of open pollination, 'KMN01' demonstrated a whiter bark, upright form, and leaves that appeared uncharacteristic of the surrounding trees. The specimen was uprooted and replanted in the inventor's residential yard in Bonners Ferry, where it was observed for a number of years. 'KMN01' maintained its upright form without any pruning. 'KMN01' has a fall-season coloration transitioning from green, to yellow, to orange, and in some years, red.

In April 2011, after observing the consistent presentation of characteristics that were originally selected for, the inventor planted 200 seedlings of *Populus tremuloides*. Then in August of the same year, the inventor budded all 200 aspen with the buds from the discovered plant 'KMN01'. By August 2012, one hundred and sixty of the budded aspen were four to eight feet (1.2 to 2.4 meters) tall. Further to this successful propagation, the inventor budded an additional 300 ramjets from the discovered 'KMN01'. This testing and repeated propagation demonstrated that the distinct characteristics herein are true to type and transmissible by asexual reproduction with uniformity and stability.

BRIEF SUMMARY OF THE INVENTION

The following traits represent the characteristics of the new variety 'KMN01'. These traits in combination distinguish this variety from all other commercial varieties known to the inventor.

1. Orange to red fall color;
2. Upright branching habit;
3. Disease resistance to *Venturia* leaf and shoot blight;
4. Spring new growth is bronze to red in coloration;
5. Bright white bark; and
6. The variety is seedless.

Plant Breeder's Rights for this variety have not been applied for and 'KMN01' has not been offered for sale more than a year before the filing date of this application. 'KMN01' has not been promoted under any other breeder's reference or cultivar name.

Plants of 'KMN01' have not been observed under all possible environmental and cultural conditions. The phenotype may vary somewhat with variations in environmental conditions, for example, with fluctuation in temperature, soil chemistry, and photoperiod without, however, any variance in genotype. The following observations and characteristic data disclosed were collected in the Spring of 2014 in Bonners Ferry, Id. unless otherwise indicated.

BRIEF DESCRIPTION OF THE PHOTOGRAPH(S)

The accompanying colored photographs illustrate the overall, typical appearance of the new and distinct aspen tree showing the colors as true as it is reasonably possible to obtain in colored reproductions of conventional photography. Due to color variation reproduced in the photographs, color characteristics of this new variety should be determined with reference to the observations described herein, rather than a reliance on the photographs alone. Photographs are taken over a number of years and include the originally discovered tree as well as ramets at one and two years. The different photographs are intended to represent the distinctive characteristics of 'KMN01'.

FIG. 1 (Oct. 2, 2008), demonstrates the red leaf coloration in the Fall for 'KMN01' at 5 years-old.

Figure 2:
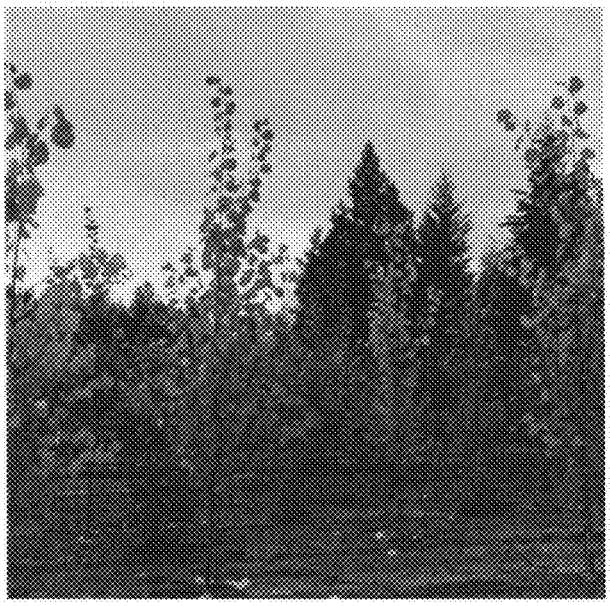

FIG. 2 (Oct. 27, 2013), a 2 year-old tree budded from 'KMN01' demonstrates the upright form and orange to red fall-season coloration.

Figure 3:
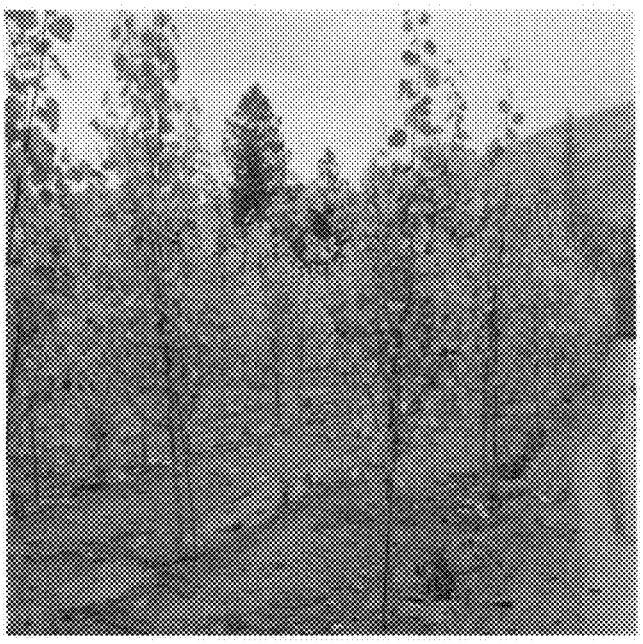

FIG. 3, demonstrates the semi-columnar shape typical of the invention.

Figure 4:
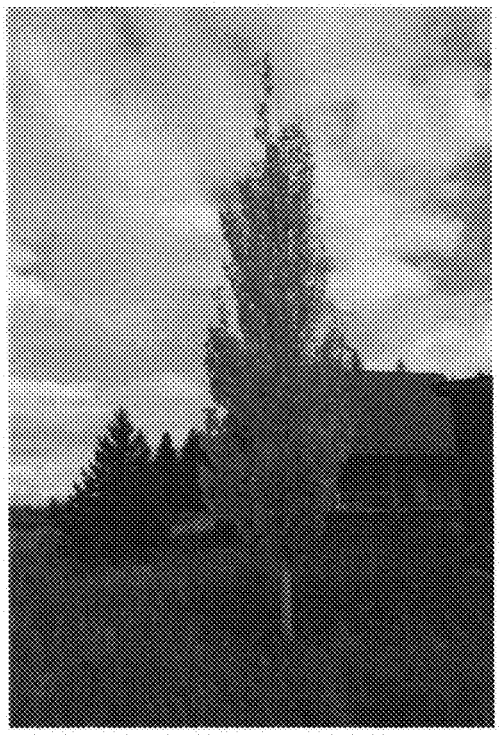

FIG. 4 (Oct. 24, 2011), demonstrates orange Fall season color and the bright white bark at 8 years-old.

Figure 5:
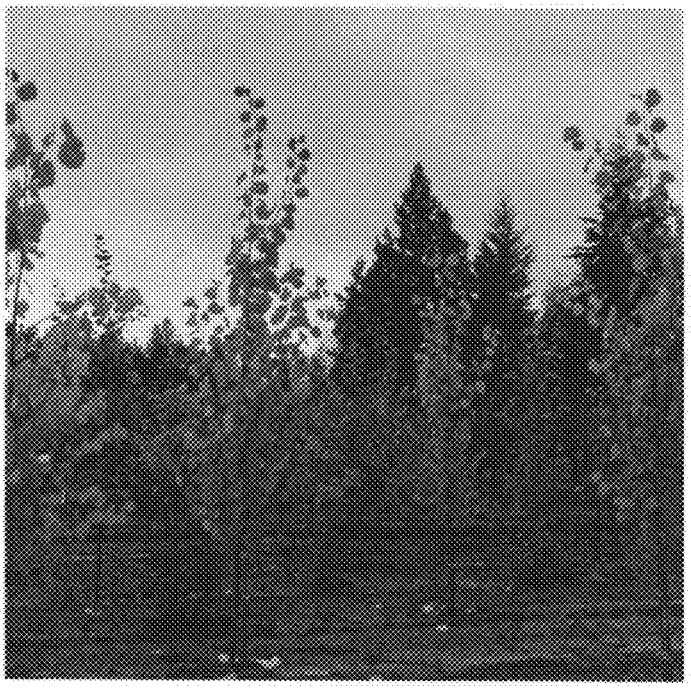

FIG. 5 (Oct. 27, 2013), represents the largest specimens of the trees budded from 'KMN01' (show here at two years-old).

Figure 6:
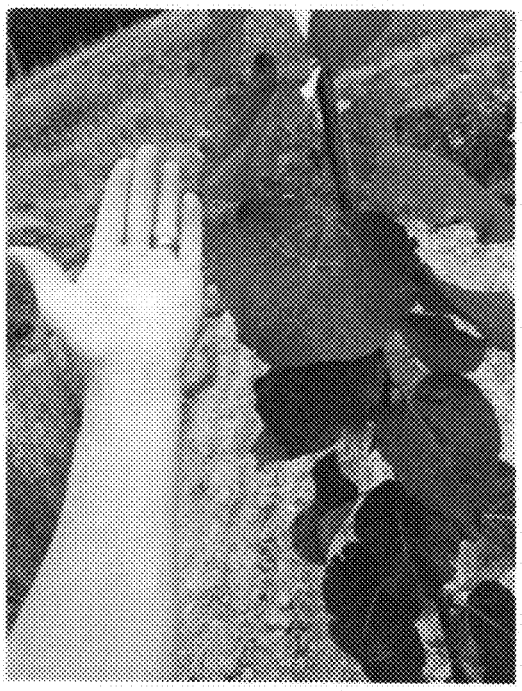

FIG. 6 (Aug. 3, 2013), a one year-old budded plant, demonstrates the leaf size in comparison to an adult human arm.

Figure 7:
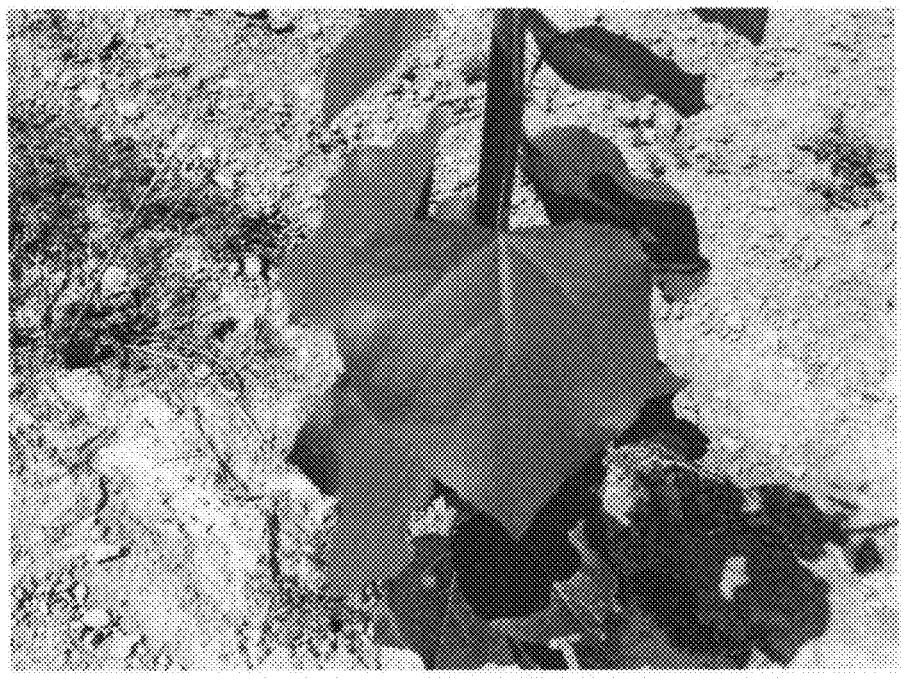

FIG. 7 (Aug. 3, 2013), a one year-old budded plant, demonstrates the leaf morphology.

Figure 8:
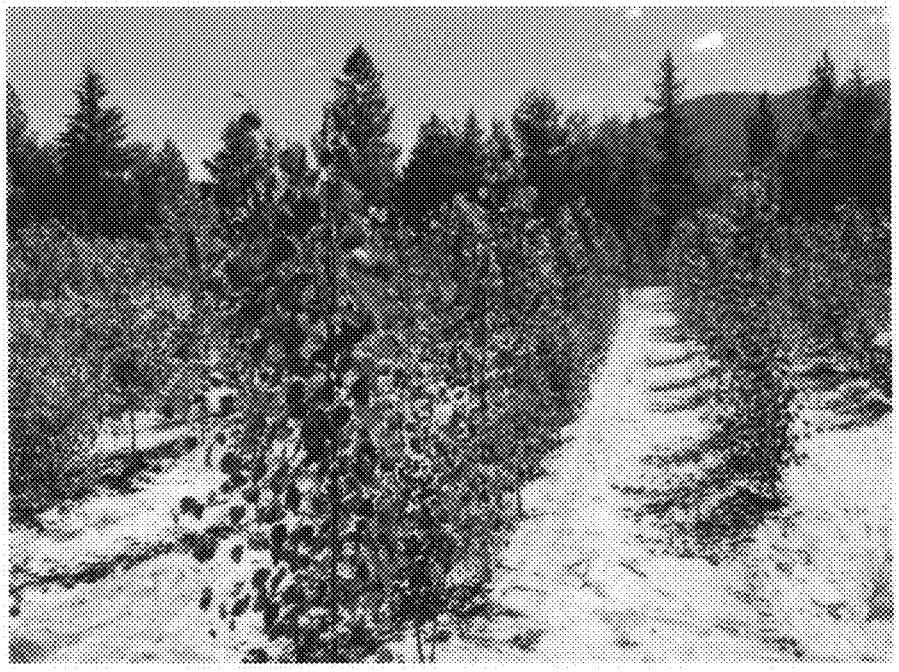

FIG. 8 (Jun. 10, 2013), representing two year-old un-pruned plants budded from 'KMN01', demonstrates their upright branching habit.

DETAILED BOTANICAL DESCRIPTION

The following is a detailed description of the new variety 'KMN01'. Data was collected from a plant approximately two years-old and from three year-old rootstock in the Spring (April) 2014. The color determinations are in accordance with the 2007 edition of The Royal Horticultural Society Colour Chart published by The Royal Horticultural Society (London, England), except where general color terms of ordinary dictionary significance are used and color readings were observed under natural, outdoor light.

TABLE 1

| VARIETY DESCRIPTION |
|---|
| Classification: |
| Family: Salicaceae<br>Botanical: *Populus tremuloides*<br>Common: Trembling Aspen<br>Parentage: |
| Parent One: A commercially available, unnamed *Populus tremuloides* (unpatented)<br>Parent Two: Unknown |

TABLE 1-continued

| VARIETY DESCRIPTION |
|---|
| Propagation: |
| Budding and sucker harvest from parent plant<br>Plant: |
| Height, unpruned (m): 4.22 meters<br>Vigor: Optimal<br>Shape: Pyramidal to semi-columnar<br>Growth rate: Rapid (19.05 mm diameter per year) taken from 152.4 mm from ground<br>Growth habit: Upright<br>Crown width (m): 0.83 meters<br>Crown height (m): 3.96 meters<br>Crown shape: Semi-columnar<br>Crown volume (m3): 0.7 $m^3$<br>Trunk and Branches: |
| Trunk diameter (cm): 3.81 cm taken at 15.24 cm above the ground<br>Trunk texture: Smooth with powder on bark<br>Trunk bark color: RHS Black Group 202D<br>Tree bark depth (mm): 2 mm<br>Tree bark furrows: None observed<br>Branch length (m): 0.89 m (measured from trunk, along upper branch surface on a branch located at mid-crown)<br>Branch texture: Smooth<br>Branch color: RHS Greyed-Green Group 198A<br>Branch arrangement: Alternate<br>Crotch angle from main trunk: 27°<br>Burl: None observed<br>Scion/rootstock: |
| Scion circumference/rootstock circumference ratio: 13.5 cm to 16.5 cm (of 3-year-old rootstock)<br>Height at which scion measurement is taken: 4.0 cm from ground<br>Bud-union characteristics: Slight wave from rootstock to scion on the bud union<br>Time to initiate roots (average): 14 days<br>Time to produce a rooted plant (average): 6 months<br>Height at which rootstock measurement is taken: 2.5 cm from ground<br>Suckering: None observed on two-year-old invention plants. Suckering from roots at year ten, on discovered plant.<br>Leaves: |
| Size:<br>a. Length (mm): 62.0 mm<br>b. Width (mm): 56.0 mm<br>Type: Simple<br>Shape: Broadly ovate<br>Apex: Acute<br>Base: Obtuse<br>Margin: Sinuate to Serrate<br>Cross section: Flat<br>Venation: Each leaf has a central primary vein, which runs to the apex of the leaf. Secondary veins initiate from the primary vein at a 28 degree angle in the apex direction of the leaf, and eventually spreading to other, smaller veins to form a network of netted veins<br>Surface: |
| a. Upper surface texture: Glabrous, smooth<br>b. Lower surface texture: Reticulate netted veins<br>c. Upper surface color: RHS Green Group N137A<br>d. Lower surface color: RHS Green Group 137C<br>Leaf bud: |
| a. Shape (both immature and mature): Imbricate, conical, and sharp-pointed<br>b. Texture: Smooth, slightly resinous<br>c. Color:<br>Immature: RHS Green Group 143A<br>Mature (before opening): RHS Greyed-Orange 166B<br>d. Length (mm):<br>Immature: 9.0 mm<br>Mature: 12.0 mm<br>e. Width (mm):<br>Immature: 3.0 mm<br>Mature: 4.0 mm |

TABLE 1-continued

| VARIETY DESCRIPTION |
|---|
| Petiole: |
| a. Shape: Oval and flat on upper and lower surfaces<br>b. Color: RHS Yellow-Green Group 146B<br>c. Thorns, Spines: Absent<br>d. Length (mm): 30.0 mm<br>e. Width (mm): 1.5 mm<br>f. Texture: Glabrous<br>Cones: None observed<br>Flowers: None observed<br>Petal: None observed<br>Reproductive Organs: None observed<br>Fruit: None observed<br>Best mode growing conditions: |
| Soil conditions: Loam with a pH range from 5.0 to 7.5<br>Water use/drought tolerance: Drought tolerant, specimen current growing without irrigation; however, while the tree will grow in hot and dry conditions, it will grow most rapidly with soil moisture<br>Resistance to disease: Disease resistance to *Venturia* leaf and shoot blight |

COMPARISON TO SIMILAR VARIETIES

Parent One, a commercially available, unpatented and unnamed variety of *Populus tremuloides*, producing seed and presenting branching angles of 55 degrees with serrate leaf blade margins. In contrast, 'KMN01' is seedless, is more upright in form, with a branching angle of 27 degrees, and has sinuate to serrate leaf blade margins.

Parent Two is unknown; therefore, no comparison can be made.

The commercially available *Populus tremuloides* named 'Driefest' (unpatented) produces seed, has a silver bark color and a branch angle from the stem at 16 degrees. In contrast, 'KMN01' is seedless, has white bark color and a branching angle from stem at 27 degrees.

I claim:

1. A new and distinct variety of *Populus tremuloides* having the characteristics substantially as described and illustrated herein.

* * * * *